(12) United States Patent
Sears et al.

(10) Patent No.: US 7,438,724 B2
(45) Date of Patent: Oct. 21, 2008

(54) SYSTEM AND METHOD FOR FORCE FEEDBACK

(75) Inventors: Harold H. Sears, Salt Lake City, UT (US); Arthur D. Dyck, Draper, UT (US); Edwin K. Iversen, Holladay, UT (US); Steven R. Kunz, Salt Lake City, UT (US); James R. Linder, West Jordan, UT (US); Shawn L. Archer, Salt Lake City, UT (US); Reed H. Grant, Salt Lake City, UT (US); Ronald E. Madsen, Jr., Salt Lake City, UT (US)

(73) Assignee: Motion Control, Inc., Salt Lake City, UT (US)

( * ) Notice: Subject to any disclaimer, the term of this patent is extended or adjusted under 35 U.S.C. 154(b) by 0 days.

(21) Appl. No.: 11/011,759

(22) Filed: Dec. 13, 2004

(65) Prior Publication Data

US 2005/0192676 A1    Sep. 1, 2005

Related U.S. Application Data

(60) Provisional application No. 60/529,328, filed on Dec. 12, 2003.

(51) Int. Cl.
*A61F 2/48* (2006.01)
*A61F 2/66* (2006.01)
*B25J 19/02* (2006.01)

(52) U.S. Cl. .............................. 623/24; 623/57; 414/5; 901/33; 901/34

(58) Field of Classification Search .................. 623/24, 623/25, 26, 57, 58, 59, 60, 61, 62, 63, 64, 623/65; 414/5; 901/33, 34
See application file for complete search history.

(56) References Cited

U.S. PATENT DOCUMENTS

| | | | | |
|---|---|---|---|---|
| 2,656,545 A | * | 10/1953 | Conzelman, Jr. et al. | 623/57 |
| 3,751,733 A | * | 8/1973 | Fletcher et al. | 623/24 |
| 4,808,187 A | * | 2/1989 | Patterson et al. | 623/25 |
| 4,831,531 A | * | 5/1989 | Adams et al. | 701/2 |
| 5,413,611 A | * | 5/1995 | Haslam et al. | 623/25 |
| 5,888,213 A | * | 3/1999 | Sears et al. | 623/24 |
| 6,088,017 A | * | 7/2000 | Tremblay et al. | 345/156 |
| 6,275,213 B1 | * | 8/2001 | Tremblay et al. | 345/156 |
| 7,006,895 B2 | * | 2/2006 | Green | 700/245 |

* cited by examiner

*Primary Examiner*—Thomas J Sweet
(74) *Attorney, Agent, or Firm*—Thorpe North & Western LLP

(57) ABSTRACT

A system and method of grip force feedback for use with a prosthetic device is provided in the present invention. The system can include a prosthetic hand having a plurality of digits for use with the prosthetic device. A force sensor can be provided to produce a force signal and the force sensor is configured to be associated with the plurality of digits for the prosthetic hand. In addition, a force feedback controller can receive the force signal from the force sensor. A force feedback actuator is also in communication with the force feedback controller. The force feedback actuator can provide feedback vibrations to a user of the prosthetic device.

9 Claims, 8 Drawing Sheets

Percent Error from Target Force

|  | 15 lbs | 10 lbs | 5 lbs |
|---|---|---|---|
| Volunteer 1 | | | |
| no feedback | 41 | 72 | 90 |
| with feedback | 13 | 10 | 42 |
| Volunteer 2 | | | |
| no feedback | 11 | 39 | 52 |
| with feedback | 9 | 16 | 16 |
| Volunteer 3 | | | |
| no feedback | 17 | 46 | 24 |
| with feedback | 10 | 7 | 16 |

|  | 5 lbs | 10 lbs | 15 lbs |
|---|---|---|---|
| no feedback (avg) | 55 | 52 | 23 |
| with feedback (avg) | 25 | 11 | 11 |

SYSTEM AND METHOD FOR FORCE FEEDBACK

This application claims priority to the U.S. Patent Application 60/529,328 filed on Dec. 12, 2003 and entitled SYSTEM AND METHOD FOR GRIP-FORCE FEEDBACK.

FIELD OF THE INVENTION

The present invention relates generally to force feedback in a prosthetic hand.

BACKGROUND

There are approximately 100,000 individuals with an arm absence or complete hand absence in the United States, and perhaps as many as 10,000 new cases each year. Electric hands are becoming more widely adopted as the commercially available components have become more dependable and the function of electric prostheses has improved. Some market studies indicate that, in the clinics specializing in upper limb prosthetics, electric hands may be used in at least one-half of the new prosthetic fittings. Contributing to this trend, training for prosthetists in fitting skills and techniques is part of the curriculum of accredited programs and is widely provided by manufacturers.

Prosthetic hands and arms that are powered can be controlled by using myoelectric control. Myoelectric control is an effective, comfortable and natural way to control artificial arms and hands. Small, stainless-steel electrodes are placed on the skin and sense the electrical activity of the muscles using the electromyographic signals. These muscle signals are electronically amplified and used to move the hand as desired.

The electrodes are installed in the prosthesis socket when the arm is fitted, then connected to the electronics of the prosthetic arm and/or hand system. Retraining of the patient's muscles may also be needed to build strength and control. Some types of myoelectric systems use proportional control, where the amputee can move the hand slowly or quickly, instead of simply turning it on and off. A high sensitivity in the prosthetic system provides a more natural response with less effort.

Current electric hands or terminal devices (TDs) do not generally provide the wearer any direct feedback or sensation about the pinch force generated by the hand. Individuals who have not lost a hand or limb do not realize the importance of being able to sense how hard or soft an item is being handled. A natural hand provides detailed feedback using an extensive nerve network in the skin and other related information can be provided using the muscles. Without this feedback, it can be easy to damage objects that are handled with a prosthetic hand.

Body-powered TDs can give the wearer a very limited amount force sensation and proprioception through the cable force and position. Unfortunately, harnessed feedback uses more harnessing and a control cable, which in turn causes discomfort to the prosthesis wearer.

In comparison, an electric prosthesis does not provide feedback regarding the powered grip or movement of the prosthetic. With an electric hand, the wearer's control over pinch force is only approximate and depends heavily upon visual feedback. Using visual feedback is not easy when an object is hidden from view inside the hand or is viewed in dim light. In addition, visual feedback is not generally helpful when the resistance of a hard or soft object is not known in advance. In other words, soft objects can sometimes appear hard but then when force is applied the prosthesis user may quickly find out visually that the soft object has been damaged.

SUMMARY OF THE INVENTION

A system and method of force feedback for use with a prosthetic device is provided in the present invention. The system can include a prosthetic hand having a plurality of digits for use with the prosthetic device. A force sensor can be provided to produce a force signal and the force sensor is configured to be associated with the plurality of digits for the prosthetic hand. In addition, a force feedback controller can receive the force signal from the force sensor. A force feedback actuator is also in communication with the force feedback controller. The force feedback actuator can provide feedback vibrations to a user of the prosthetic device.

DETAILED DESCRIPTION

Figure 1:
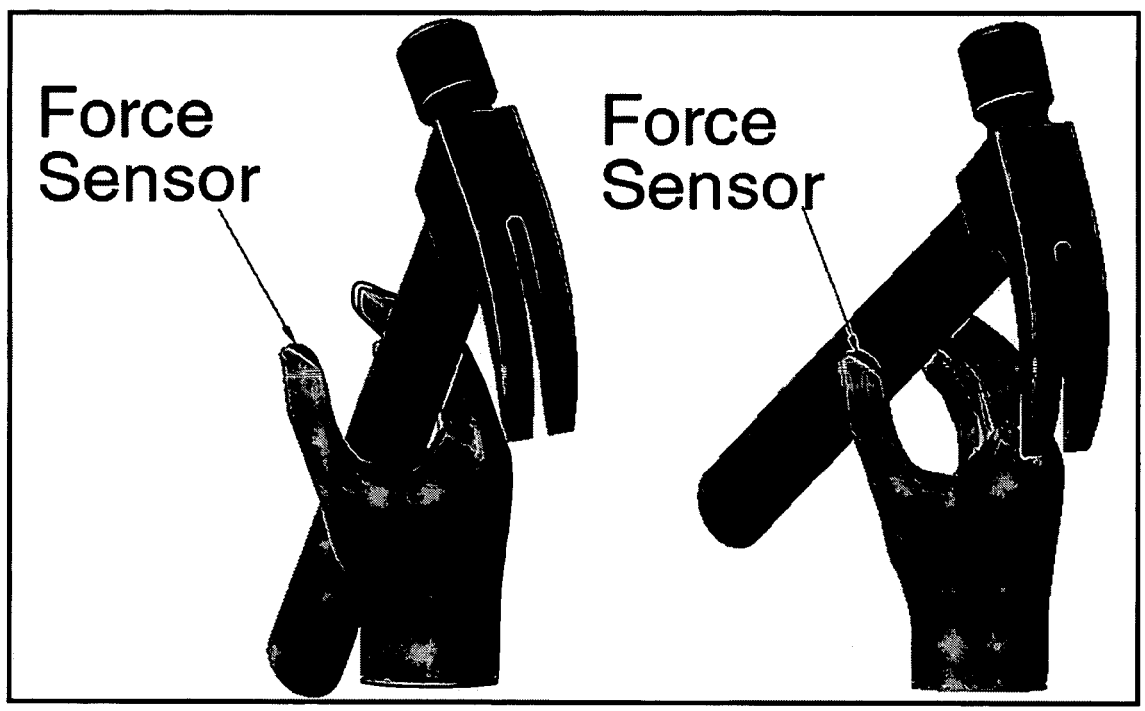
FIG. 1 depicts a prosthetic hand having a sensor at a finger tip.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

The present invention includes a system and method for grip and touch force feedback. The force feedback system can include a force sensor, a force feedback actuator, and a force feedback controller. A force of the user or amputee gripping an object can be measured using sensors in the prosthetic hand. Then force feedback can be provided to the user of the prosthetic limb or amputee. The purpose of the force feedback is to present grip and touch force to the prosthesis user in a way that will aid in prehension. The present discussion will first address sensing systems and methods, and then a discussion of embodiments of the present invention will follow.

The system and method used for sensing force with a prosthetic device affects the accuracy of force feedback for a prosthetic device. One valuable force sensing configuration may be a large number of sensors along the full surfaces of the fingers, so that both the point of contact and the magnitude and direction of the applied forces and torques can be measured. Such a configuration can more approximately simulate the body's own nerve sensing system. However, this approach is generally impractical at this time because of the size of commercially available sensors and problems with wiring and signal processing.

An alternative method is to provide a force measurement for gripping and touch based on fingertip force measurement. Using finger tip normal forces alone may be useful when used with the appropriate calculations and extrapolations. However, using finger tip forces can miss forces applied to grasped objects by the fingers proximal to the fingertips. FIG. 1 illustrates how fingertip sensors alone will not generally measure grip force on objects grasped proximal to the fingertips. An amputee who uses a prosthetic device will often grasp an object using the sides of the thumb and finger instead of just the fingertips alone. Without force sensing to aid in controlling the grasping of an object using the area proximal to the fingertips, an amputee can easily crush or damage items.

In an exemplary embodiment of the present invention, grip and touch force measurements are based on thumb reaction loads. Measuring loads using sensors at the base of the thumb has certain advantages. One advantage is that all grip and touch forces applied by any part of the grasped object or the opposing fingers will produce reaction loads on the thumb.

Force measurement based on thumb reaction loads alone are a comparatively good measurement of finger and thumb moments, but are not necessarily a good measurement of applied forces. This is because the point of applied force is not known. If the point of load application is assumed by the controller to be the finger tips, and if the controller is trying to control actual grip forces applied by the middle or base of the finger, those forces will be greater than desired. However, when a force controller is attempting to control finger moments, then knowing a contact point is not necessary. One or more sets of sensors at the base of the thumb can respond to loads applied by any of the fingers and at any point along the surface of the fingers. Using sensors at the base of the thumb also measures thumb torques accurately.

Alternative methods for measuring forces for the fingers of a prosthetic hand but be used in combination with elements of the present invention. For example, fingertip sensors can be used to provide information to the controller to calculate the net torque on the fingers. Each fingertip sensor may sense normal and shear forces. The net finger torque may be calculated as a function of these measured forces. The total force on an object can then be derived knowing the points of contact.

Figure 2:
FIG. 2 illustrates strain gauges at a base of a thumb in a prosthetic hand in accordance with an embodiment of the present invention.

FIG. 2 illustrates an example location of a thumb reaction sensor in a prosthetic hand. In this embodiment, objects grasped proximal to the fingertips will experience more contact force for the same finger torque than an object grasped at the fingertips. However, fewer sensors can be used at the base of the thumb which decreases the overall cost of an already expensive prosthetic limb.

Figure 3:
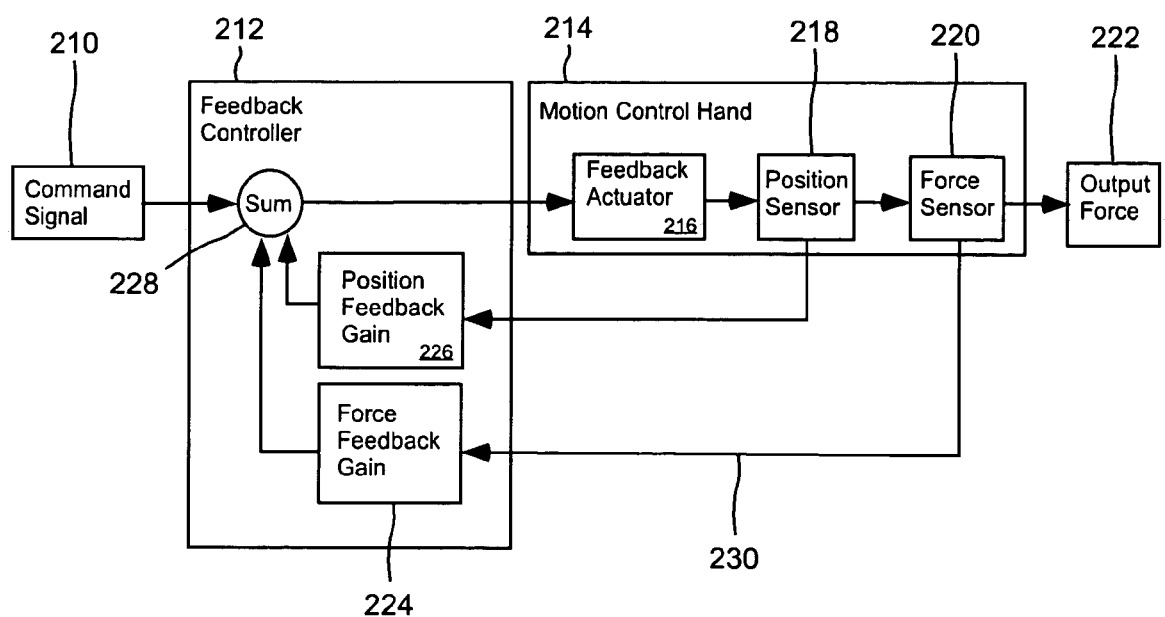
FIG. 3 is a block diagram illustrating a force feedback system for a prosthetic limb in an embodiment of the present invention.

FIG. 3 illustrates a force feedback system for use with a prosthetic device. The force feedback system can comprise a prosthetic hand having a plurality of digits for use with the prosthetic device. A command signal 210 is initially received from a user of the prosthetic device to control the movement and force of the prosthetic device. Once the prosthetic device receives the user commands, a certain output force 222 can be delivered. A force sensor 220 is configured to produce a force feedback signal 230 and the force sensor is configured to be associated with the plurality of digits for the prosthetic hand. As discussed before, one example of a location for the force sensor is at the base of a thumb. A force feedback controller 212 can then receive the force signal 226 from the force sensor. In addition, the force sensor sends the force signal through a force feedback gain 224.

The force feedback controller 212 drives the force feedback actuator 216 such that a feedback force and/or vibrations are provided for a user. The feedback force can be a function of the actual measured grip and/or touch force. In general terms, the more force the user applies, the more the force feedback actuator can be set to vibrate. In addition, a device position sensor 218 can also be provided and the device position sensor can send position signals back to a position feedback gain module 226. The combination of the position and force feedback gain signals are fed back into a summing module 228. This feedback can help control the amount of feedback provided and the amount of output force 222 supplied by the prosthetic device.

To reduce any unwanted effects of drive friction, a force servo loop can be utilized. The control signal from the prosthesis user provides the command signal 210 to the outer position loop. An output force signal is then used to control the output force 222 for the prosthesis device.

A number of systems and methods for providing the force feedback can be provided in the present invention. In one example embodiment, an electric motor with eccentric mass on the shaft can be used. The electric motor(s) can be driven in proportion to the amount of force applied by the user of the prosthetic hand. When the motor speed increases, then the motor provides increased feedback vibrations due to the eccentric mass on the motor shaft. The feedback vibrations represent the present grip and touch force of the prosthetic device for the user as determined by the force sensor and feedback system.

Figure 8:
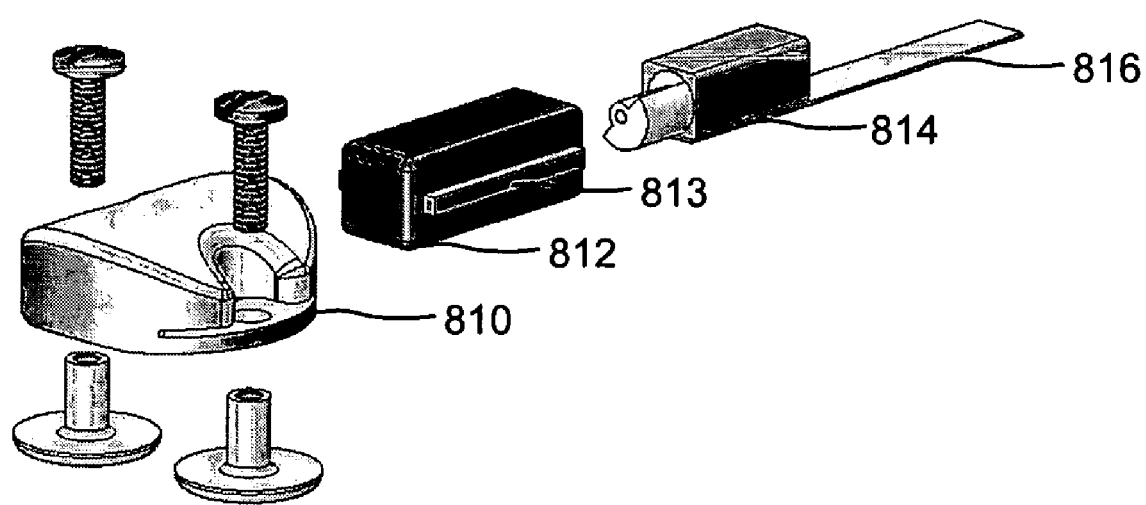
FIG. 8 illustrates an exploded view of an embodiment of the invention that provides feedback vibrations using a motor with an eccentric weight in a flexible mount.

FIG. 8 illustrates an exploded diagram of an electric motor 814 and electrical connections 816 that are mounted on a flexible mounting base. A flexible mounting module 812 is configured to enable to electric motor to provide increased feedback vibrations. The flexible mounting module includes at least one flexible or rubberized length of material 813 to allow the electric motor to vibrate in a horizontal direction. For example, two matching flexible strips can be provided on both sides of the flexible mounting module. A hard protective enclosure 810 is provided to enclose the flexible mounting module and to enable mounting of the motor to the prosthesis.

In an alternative embodiment of the invention, a cylindrical DC motor with an eccentric mass encapsulated in a cylindrical housing can be used. The cylindrical motor can be mounted either against the skin of the prosthesis user's remnant limb, on flexible socket liner, or on a compliant mounting system such that vibrations can be sensed by the skin of the remnant limb.

Voltage can be applied to the electric motor as a function of grip and/or touch force. For example, the motor may be a DC motor that can be operated upon battery power carried by the prosthetic user. In one embodiment, the eccentric mass may be tuned so that when the mass is coupled with the compliance of the mount, the system has a resonant frequency of about 20 Hz. This frequency is generally below an audible frequency for humans. In this configuration, the frequency and amplitude of the spring/mass system increases as voltage is applied up to the resonant frequency. The electric motor with an eccentric mass can be configured to receive a voltage that increases as a function of force in order to increase the feedback vibration output from the electric motor.

If the spring mass system has a lower natural frequency (for example 5 Hz.), then as voltage is applied, the amplitude increases until the resonant frequency and then diminishes. This makes the force feedback less intuitive because the amplitude of the feedback signal is inversely proportional to force applied by the prosthetic hand or arm, but an inverse feedback can be used if desired.

Figure 4:
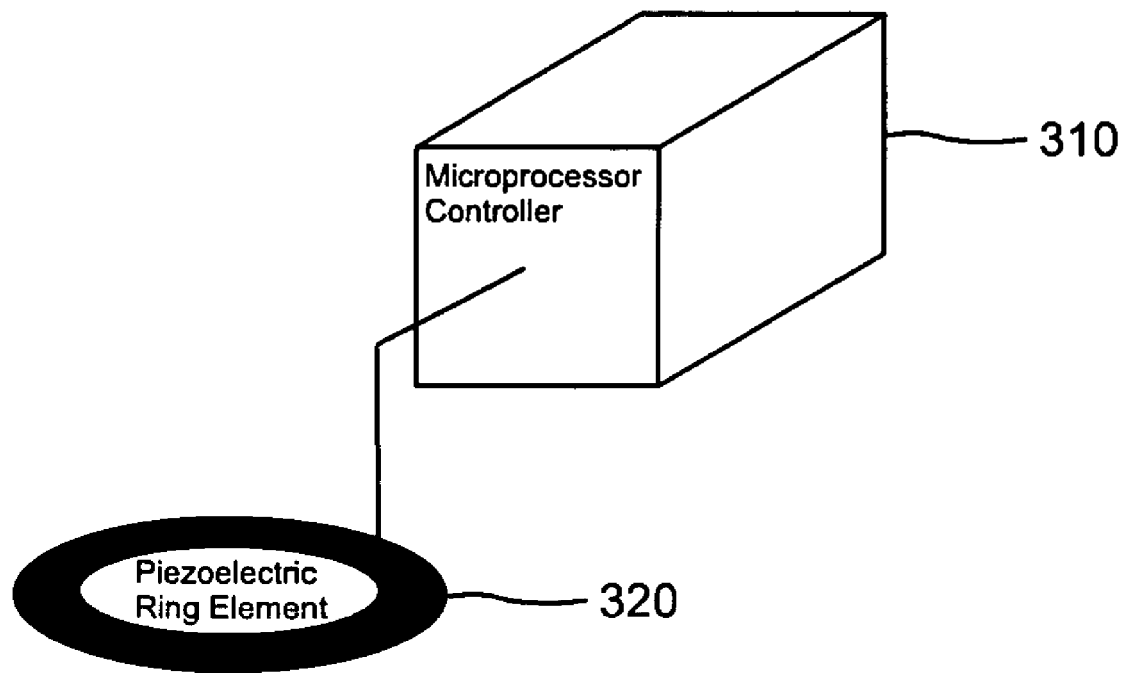
FIG. 4 illustrates a piezoelectric element for use in a prosthetic device in accordance with an embodiment of the present invention.

Another embodiment of the present invention is illustrated in FIG. 4 with a piezoelectric element force feedback device. The piezoelectric actuator 320 is comparatively compact and has a longer potential lifetime as compared to the eccentric motors. However, the piezoelectric element cannot be driven directly from the electronic circuits or microprocessor controller 310 without significantly increasing electrical capacity of the electronic circuits as compared to power used with eccentric motors.

The frequency of this piezoelectric device may be controlled as a function of grip and/or touch force. A vibrating piezoelectric element can increase in amplitude and frequency of vibration based upon the grip and touch force of the hand (i.e., the force received from one or more sensors). This method may also use more battery power than the motorized "pusher" which will be discussed later.

Figure 5:
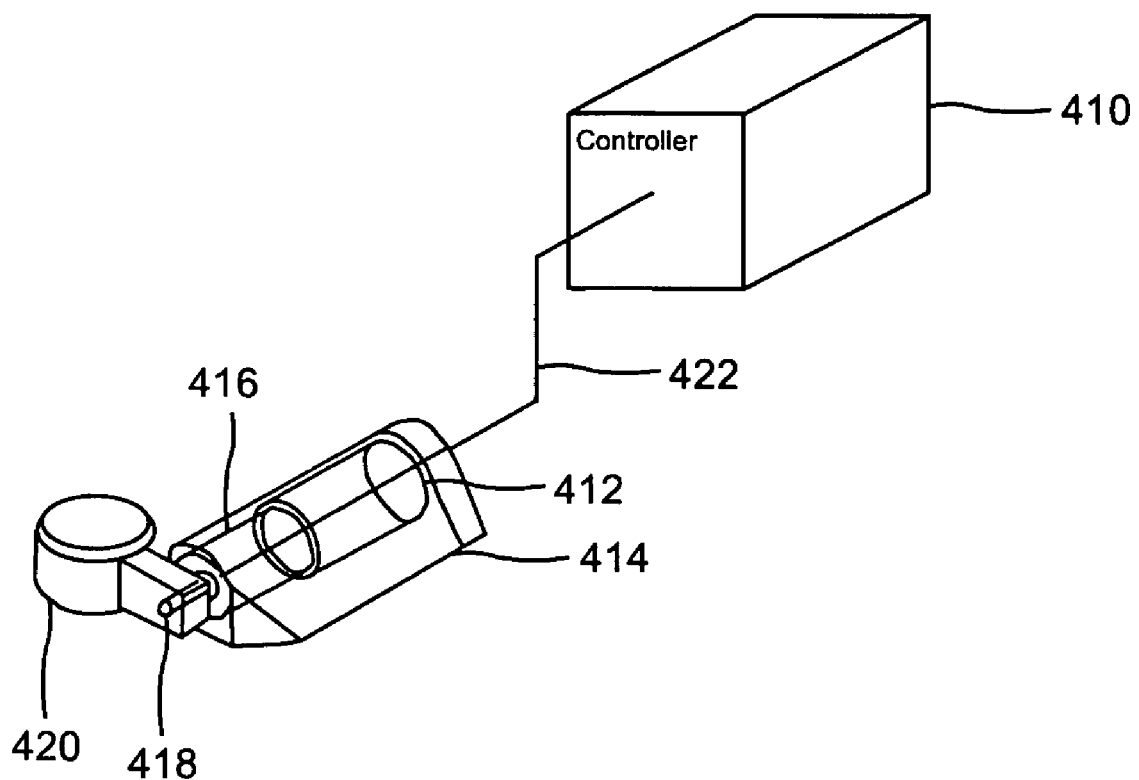
FIG. 5 illustrates a skin pushing device in an embodiment of the invention.
Figure 6:
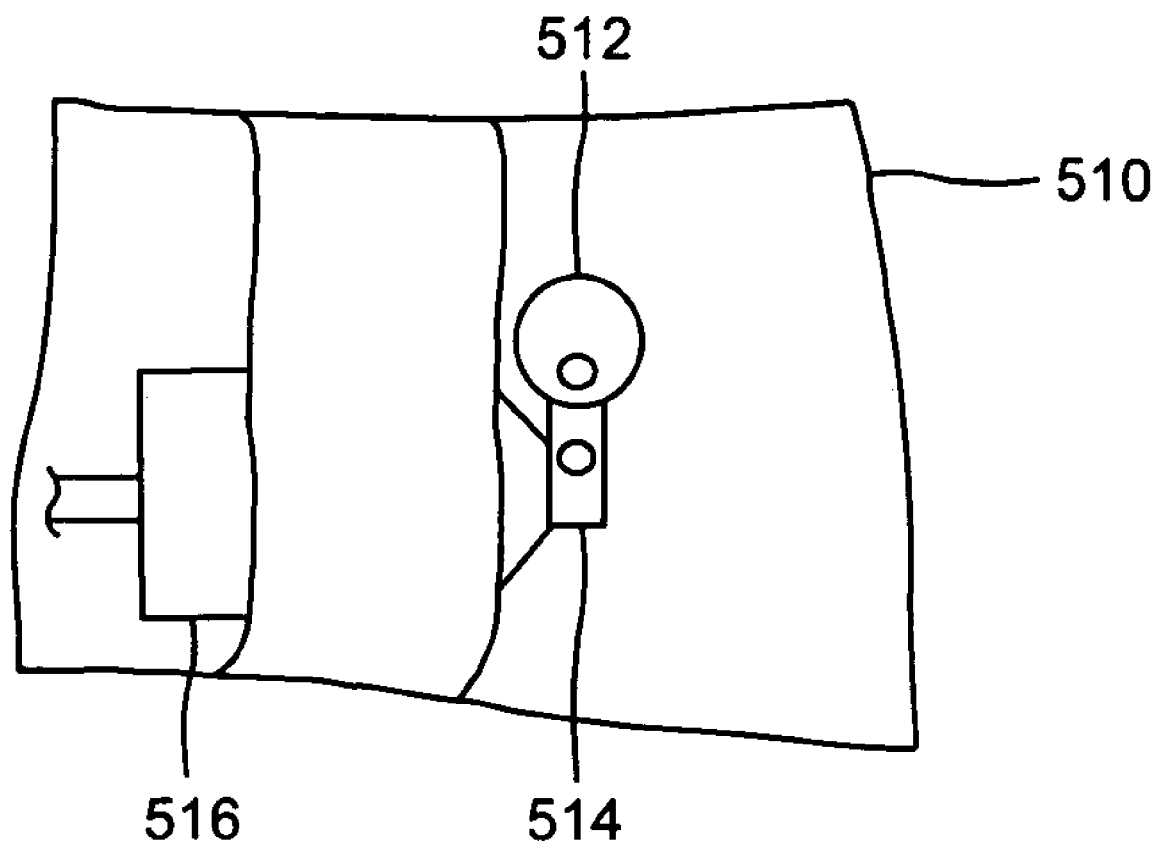
FIG. 6 illustrates an additional configuration of a skin pushing device with a circular tip in an embodiment of the present invention.

FIGS. 5 and 6 illustrate grip and touch force feedback using a motorized "pusher." This pusher system operates by having the pusher portion of the device vibrate or tap on the skin of the amputee. This system consists of a motorized drive which is back drivable, a lever, and a "skin pusher" tip. The motor can be powered as a function of the measured sensor force. The tip will therefore apply an oscillating or periodic load to the user's remnant limb at a rate in proportion to the sensor force. The soft tissue of the remnant limb can return the tip to the zero force position by back driving the motorized drive.

A force feedback system is illustrated in FIG. 5 for use with a prosthetic device. The force feedback system can comprise a prosthetic hand having a plurality of digits and a force sensor located substantially near the base of the thumb of the prosthetic hand. A force feedback controller 410 can be configured to receive a force signal from the force sensor (not shown). A force feedback pusher 420 can be indirectly driven by the force feedback controller. As a result, the force feedback pusher can provide a periodic or vibrating pushing to the user's skin engaged by the prosthetic device, and the force feedback can be based on the force signal 422. In addition, FIG. 5 illustrates a motor 412 located in a mounting base 414 that receives the interpreted force signal. A gearbox 416 and shaft 418 can connect the force feedback pusher to the controller.

One reason for using a back drivable motor is that it allows the force feedback pusher to quickly and repeatedly touch or vibrate on the user's skin. When a non-backdrivable motor is used, then the amputee or user of the prosthesis can become "immune" to the constant force of the feedback pusher.

FIG. 6 illustrates an alternative embodiment of the invention where the pusher tip 512 is a broad tip that is larger than a driving arm 514 to which the tip is connected. In addition, the driving arm is connected to an electric motor 516 to drive the pusher tip.

Estimating the actual grip and/or touch force when both frequency and amplitude (i.e. strength) were modulated is useful to an amputee and can be comparatively intuitive for the amputee or end user of the prosthetic device. Positive results have been obtained using the feedback of the present system and method.

Figure 7:
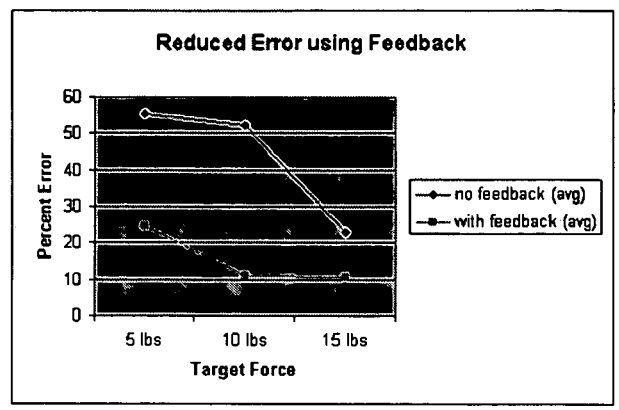
FIG. 7 is a chart illustrating improvements in the use of applied force in a prosthetic device with a feedback system.

FIG. 7 is a chart illustrating how a force feedback system improves a user's ability to control force. In this example test, subjects were asked to apply a certain amount of force measured in pounds to an object with the prosthesis. This force was measured and the difference between the actual applied force and the desired force was measured as a percentage error. The charts illustrate that force feedback increased the users' ability to reduce error in the amount of force applied by the prosthesis from anywhere between 10% to 30%. This is a clinically significant error reduction.

In another embodiment of the invention, a method is provided for grip force feedback for use with a prosthetic hand having a plurality of digits. One operation includes generating force signals using a force sensor for the prosthetic hand. The force feedback controller can then receive force signals from the force sensor. A further operation is driving a force feedback actuator based on the force signals received from the force feedback controller. This can result in supplying feedback vibrations to a user of the prosthetic device based on the force signals received from the force feedback actuator. These feedback vibrations can be supplied using a force feedback actuator that is an electric motor with an eccentric mass. The feedback vibrations supplied can be of an intensity that are calculated as a function of the force signals received.

It is to be understood that the above-referenced arrangements are only illustrative of the application for the principles of the present invention. Numerous modifications and alternative arrangements can be devised without departing from the spirit and scope of the present invention. While the present invention has been shown in the drawings and fully described above with particularity and detail in connection with what is presently deemed to be the most practical and preferred embodiment(s) of the invention, it will be apparent to those of ordinary skill in the art that numerous modifications can be made without departing from the principles and concepts of the invention as set forth herein.

The invention claimed is:

1. A force feedback system for use with a prosthetic device, comprising:
   a prosthetic hand having a plurality of digits for use with the prosthetic device;
   a force sensor configured to produce a force signal, the force sensor being configured to be associated with the plurality of digits for the prosthetic hand;
   a force feedback controller configured to receive the force signal from the force sensor;
   a force feedback actuator in communication with the force feedback controller, the force feedback actuator having an electric motor with an eccentric mass encapsulated within a motor housing, the electric motor configured to receive a voltage applied that increases as a function of force so that the voltage increases as the resonant frequency of the electric motor decreases, in order to provide feedback vibrations to a remnant limb on a user of the prosthetic hand which are inversely proportional to the force signal; and
   a compliant mounting system to couple the prosthetic hand to the remnant limb.

2. A force feedback system as in claim 1, wherein the feedback vibrations represent a current grip force of the prosthetic device for the user as measured by the force sensor.

3. A force feedback system as in claim 1, wherein the electric motor is mounted on a flexible mount to enable to electric motor to provide increased feedback vibrations.

4. A force feedback system as in claim 1, wherein the force feedback actuator is an electric motor with an eccentric mass on a shaft of the electric motor.

5. A force feedback system as in claim 1, wherein the force sensor is located at a base of a thumb.

6. A force feedback system as in claim 1, wherein the force sensor measures the magnitude and direction of applied forces and torques.

7. A force feedback system as in claim 6, wherein the force feedback controller calculates the net torque on a digit for the force sensor.

8. A force feedback system as in claim 7, wherein the net torque is a function of the normal and shear forces.

9. A force feedback system as in claim 1, wherein the force sensor can measure normal and shear forces.

* * * * *